(12) United States Patent
Shang

(10) Patent No.: US 11,298,007 B2
(45) Date of Patent: Apr. 12, 2022

(54) OPTICAL FIBER GUIDEWIRE, DETECTION SYSTEM WITH OPTICAL FIBER GUIDEWIRE AND DETECTION METHOD USING OPTICAL FIBER GUIDEWIRE

(71) Applicant: Hua Shang, Jiangsu Province (CN)

(72) Inventor: Hua Shang, Jiangsu Province (CN)

(73) Assignee: Hua Shang, Jiangsu Province (CN)

( * ) Notice: Subject to any disclaimer, the term of this patent is extended or adjusted under 35 U.S.C. 154(b) by 0 days.

(21) Appl. No.: 17/396,884

(22) Filed: Aug. 9, 2021

(65) Prior Publication Data

US 2022/0061633 A1 Mar. 3, 2022

Related U.S. Application Data

(63) Continuation of application No. PCT/CN2020/134571, filed on Dec. 8, 2020.

(30) Foreign Application Priority Data

Aug. 31, 2020 (CN) .......................... 202010894817.3

(51) Int. Cl.
*A61B 1/005* (2006.01)
*A61B 1/07* (2006.01)
*A61M 25/09* (2006.01)
*A61M 25/01* (2006.01)

(52) U.S. Cl.
CPC ............. *A61B 1/0056* (2013.01); *A61B 1/07* (2013.01); *A61M 25/0152* (2013.01); *A61M 25/09* (2013.01); *A61M 2025/09075* (2013.01)

(58) Field of Classification Search
CPC .... A61B 1/0056; A61B 1/07; A61M 25/0152; A61M 25/09; A61M 2025/09075
See application file for complete search history.

(56) References Cited

U.S. PATENT DOCUMENTS

| | | | |
|---|---|---|---|
| 10,149,720 B2* | 12/2018 | Romo | A61M 25/0138 |
| 2002/0009275 A1* | 1/2002 | Williams | A61B 90/36 |
| | | | 385/123 |
| 2016/0199620 A1* | 7/2016 | Pokorney | A61M 25/09033 |
| | | | 600/585 |
| 2017/0146453 A1* | 5/2017 | Giles | A61B 5/0084 |
| 2018/0264230 A1* | 9/2018 | Funk | A61M 25/09 |
| 2019/0183458 A1* | 6/2019 | Imai | A61B 5/6851 |
| 2020/0026062 A1* | 1/2020 | Schuster | G02B 23/2469 |
| 2020/0129740 A1* | 4/2020 | Kottenstette | A61B 34/30 |
| 2021/0161397 A1* | 6/2021 | Razack | A61B 5/6852 |

* cited by examiner

*Primary Examiner* — Daniel L Cerioni
*Assistant Examiner* — Raymond P Dulman
(74) *Attorney, Agent, or Firm* — The PL Law Group, PLLC

(57) ABSTRACT

An optical fiber guidewire according to an embodiment of the present disclosure includes at least one optical fiber and a sleeve surrounding the optical fiber. The sleeve includes a functional section, a guiding section and a supporting section that are connected in sequence. An asymmetric structure is provided on the sleeve itself or the surround of the sleeve along the optical fiber. Therefore, the optical fiber guidewire provided in this disclosure has good bending performance and operability, and thus can be easily manipulated, readily enters a body cavity with a larger opening angle, and achieves self-guidance and flexible detection of the optical fiber guidewire in the body cavity, thereby improving the effect of minimally invasive interventional treatment.

12 Claims, 10 Drawing Sheets

OPTICAL FIBER GUIDEWIRE, DETECTION SYSTEM WITH OPTICAL FIBER GUIDEWIRE AND DETECTION METHOD USING OPTICAL FIBER GUIDEWIRE

CROSS REFERENCE TO RELATED APPLICATIONS AND CLAIM OF PRIORITY

The present application is a continuation application to International Application No. PCT/CN2020/134571 with an International Filing Date of Dec. 8, 2020 which claims the benefit of Chinese Patent Application No. 202010894817.3 filed in the Chinese Intellectual Property Office on Aug. 31, 2020, the entire contents of which are incorporated herein by reference.

BACKGROUND

1. Technical Field

The disclosure relates to the technical field of medical devices, in particular to an optical fiber guidewire, a detection system with an optical fiber guidewire and a detection method using an optical fiber guidewire.

2. Background

Minimally invasive interventional therapy is a medical technology that uses specific devices such as a puncture needle, guidewire or catheter under imaging guidance to accurately reach lesion sites for diagnosis and treatment without open surgery to human body. Minimally invasive interventional therapy is more and more favored by patients for its characteristic such as definite curative effect, fast recovery, strong targeting, low recurrence, no side effects, small trauma, safety and reliability, low cost and the like.

The guidewire is frequently used in clinical practice. For example, the guidewire may be used for assisting the installation of heart stents, the ablation of thrombus, and the treatment of tumor embolization. As for the interventional surgery, the safety of the guidewire comes first. Therefore, the guidewire must have many characteristics, such as flexible head portion, good compliance, no damage, high plasticity, and providing low to moderate support.

At present, the medical guidewire sold on the market is usually composed of a wire made of stainless steel in a core. Such a wire of stainless steel has multiple sections having different diameters and is formed to the medical guidewire by winding at the top end of the wire. However, these solutions will cause the guidewire to have a larger diameter, making it difficult to enter blood vessel having a small diameter.

Meanwhile, the guidewire is usually provided with a head portion that can be actively bent, in order to achieve good maneuverability in cavity of the human body. Therefore, a shape of the head portion can be changed according to the direction of the body cavity, and thus can be easy to enter smaller branch body cavity. Currently, the guidewire is mainly driven by multiple tendons, magnetic field or memory metal to guide it to follow the established route in the body cavity, which has great limitation to operations. Therefore, how to improve the operation performance, driving performance and detection performance of the guidewire has become an urgent problem to be solved.

SUMMARY

In view of the above, embodiments of the disclosure provide an optical fiber guidewire, a detection system with an optical fiber guidewire and a detection method using an optical fiber guidewire, so as to solve technical defects in the related art.

The disclosure provides an optical fiber guidewire. The optical fiber guidewire includes at least one optical fiber and a sleeve surrounding the optical fiber. The sleeve includes a functional section capable of assisting the optical fiber to emit and collect laser light, a guiding section capable of bending and a supporting section capable of supporting an advancement of the functional section and the guiding section. The functional section, the guiding section and the supporting section are connected in sequence, and the optical fiber guidewire is further provided with an asymmetric structure capable of directional bending of the optical fiber guidewire.

Optionally, the optical fiber includes, from inside to outside, a core fiber capable of transmitting laser light, a cladding layer capable of confining laser light transmission, and a sheath capable of protecting the core fiber and the cladding layer. A lens capable of transmitting laser light is arranged at an end of the functional section away from the guiding section, of the functional section of the sleeve.

Optionally, the optical fiber guidewire further includes a developing ring located between the optical fiber and the sleeve. An inner wall of the developing ring is fixedly connected to the optical fiber, and an outer wall of the developing ring is fixedly connected to the sleeve.

Optionally, the optical fiber guidewire further includes a power fiber, and the power fiber and the optical fiber are both located within the sleeve. A length direction of the power fiber and a length direction of the optical fiber are both parallel to a length direction of the sleeve.

Optionally, the optical fiber is a detecting fiber, or the optical fiber is formed by combining a detecting fiber and a treating fiber.

Optionally, a chamber is formed between the optical fiber and the sleeve. An outer surface of the sleeve is provided with a polymer layer, and an outside of the polymer layer is provided with a hydrophilic coating or a hydrophobic coating.

Optionally, the sleeve is a metal tube or a combination of a metal tube and a transparent tube.

Optionally, the guiding section and the supporting section of the sleeve are both the metal tube, and the functional section is the metal tube or the transparent tube. An outer surface on one side of the functional section is provided with a metal reflective film for reflecting laser light.

Optionally, the asymmetric structure is an asymmetric tube wall structure of the sleeve.

Optionally, the asymmetric tube wall structure is an asymmetric slit opened on the guiding section of the sleeve; the asymmetric slit is a spiral slit and has different widths on two sides of the sleeve; or the asymmetric slit is a rectangular slit and has different depths on two sides of the sleeve.

Optionally, the asymmetric tube wall structure is formed by a wall thickness on one side of the sleeve being smaller than a wall thickness of other side of the sleeve.

Optionally, the asymmetric tube wall structure is formed by a convex side and a planar side of the sleeve, or by a convex side and a concave side of the sleeve. The convex side has an arched structure.

Optionally, the optical fiber guidewire is sheathed with a guiding tube. The guiding tube is connected to a guiding rod at an end close to the functional section and is sheathed with a wing.

Optionally, the sleeve is a hypotube, has an outer diameter of 0.9-1.2 mm, and has an inner diameter of 0.6-0.8 mm.

The disclosure also provides a detection system with an optical fiber guidewire, including:

an optical fiber guidewire as mentioned above;

a control center arranged for sending control signals to an attitude controller, a pulsed detection laser, a waveform collector and a treatment laser to control a start-up, operation or shutdown of the attitude controller, the pulsed detection laser, the waveform collector and the treatment laser;

the attitude controller arranged for receiving signals sent by the control center and distance information, and driving the optical fiber guidewire to entry or exit a body cavity or move in the body cavity;

the pulsed detection laser arranged for receiving signals sent by the control center, and sending out pulsed laser light which is transmitted to the body cavity through the optical fiber guidewire and forms laser scattering with the body cavity;

the waveform collector arranged for receiving signals sent by the control center, collecting and analyzing a delayed waveform of scattered laser in the body cavity, to obtain the distance information about a distance between a wall of the body cavity and the optical fiber guidewire, and feedback the distance information to the control center.

Optionally, the detection system with the optical fiber guidewires further includes:

the treatment laser arranged for receiving signals sent by the control center, and emitting treating laser light to irradiate a lesion site through the optical fiber guidewire.

Optionally, the optical fiber of the optical fiber guidewire is connected to the pulsed detection laser, the waveform collector, and the treatment laser through an optical fiber combiner.

The disclosure also provides a detection method using the optical fiber guidewire. The detection method is characterized in that it is used in the detection system with the optical fiber guidewire mentioned above. The method includes the following operations.

The control center receives control instructions, and sends control signals to the attitude controller and the pulsed detection laser based on the control instructions.

The attitude controller receives the control signals sent by the control center, and drives the optical fiber guidewire into the body cavity based on the control signals.

The pulsed detector receives the control signals sent by the control center, emits pulsed laser light, and scatters the pulsed laser light into the body cavity via the optical fiber guidewire.

The optical fiber guidewire receives a reflected pulsed laser light and sends the reflected pulsed laser light to the waveform collector. Based on the reflected pulsed laser light, the waveform collector determines a position of the optical fiber guidewire in the body cavity.

The attitude controller controls a subsequent movement of the optical fiber guidewire based on the position of the optical fiber guidewire in the cavity, until the optical fiber guidewire reaches target site and exits the cavity after completing detection.

Optionally, the method further includes: after the optical fiber guidewire reaches the target site, the control center sends control signals to the treatment laser, and the treatment laser emits the treating laser light which is scattered to the target site through the optical fiber guidewire to treat the target site.

The optical fiber guidewire provided in this disclosure includes at least one optical fiber and a sleeve surrounding the optical fiber. The optical fiber has functions of emitting and collecting the detecting laser light. The disclosure can obtain the distance between the wall of the body cavity and the optical fiber by detecting the flight time of laser light, so as to guide the optical fiber guidewire to change the shape and attitude thereof over time, thereby realizing the self-guidance, detection and treatment of the optical fiber guidewire within body cavity. The sleeve includes the functional section, the guiding section and the supporting section which are connected in sequence. In addition, in order to improve the bending performance and operability of the optical fiber guidewire, the asymmetric structure is provided on the sleeve itself or the surround of the sleeve along the optical fiber, so that the optical fiber guidewire can be easily manipulated and readily enter the body cavity with a large opening angle, and precise detection and treatment can be carried out in the body cavity through laser transmission, thereby improving the effect of minimally invasive interventional treatment.

The detection system with the optical fiber guidewires provided by this disclosure includes the optical fiber guidewire, the control center, the attitude controller, the pulsed detection laser, and the waveform collector. Among them, the control center can send control signals to other components to coordinate and control the cooperation among these components. The attitude controller can control the optical fiber guidewire to enter or exit the body cavity or move in the body cavity, which improves the flexibility of the optical fiber guidewire during use. Through the cooperation of the pulsed detection laser, the waveform collector and the optical fiber guidewire, the relative position of the optical fiber guidewire and the wall of the body cavity can be determined by the delay of the laser light, and then the subsequent attitude and moving direction of the optical fiber guidewire can be accurately determined. The detection system with the optical fiber guidewire provided by this disclosure innovatively uses light to guide the travel of the guidewire, and has high detection efficiency and good detection effect. In addition, the detection system with the optical fiber guidewire provided by this disclosure further includes a treatment laser, which can emit a laser light for treating to irradiate a lesion site through the optical fiber guidewire, thereby improving the flexibility and efficiency of treatment.

The detection method using the optical fiber guidewire provided in this disclosure realizes the intelligent and automatic guidance of the optical fiber guidewire in the cavity through the cooperation of the control center, the attitude controller, the pulsed detector, the optical fiber guide wire and the waveform collector. The method of the disclosure is easy and convenient in operation, and greatly improves the detection efficiency and detection effect of the optical fiber guidewire. In addition, through the cooperation of the control center, the optical fiber guidewire and the treatment laser, the laser irradiation treatment can be performed to the lesion sites of the patient with high treatment efficiency and good effect, thereby improving flexibility in use and application range of the optical fiber guidewire.

DETAILED DESCRIPTION

The embodiments of the disclosure are described below with reference to the drawings.

In this disclosure, unless otherwise specified, the scientific and technical terms used herein have the meanings commonly understood by those skilled in the art. In addition, the reagents, materials and operation steps used in this disclosure belong to common reagents, materials and routine procedures widely used in the corresponding field. Furthermore, in order to better understand the disclosure, definitions and explanations of related terms are provided below.

In this disclosure, hypotube refers to a long metal tube with micro-engineering characteristics throughout the tube. It is an important component of a catheter for minimally invasive treatment and is used to dredge clogged arteries in conjunction with a balloon and a stent. The balloon of the catheter is attached to a distal end of the hypotube. The hypotube enters the human body and pushes the balloon toward the clog portion in the artery along the long tortuous blood vessel. During this operation, it is required to avoid the kinking of the hypotube, and enable it to move smoothly in the human body (propulsion, tracking and rotation).

Example 1

Figure 1:
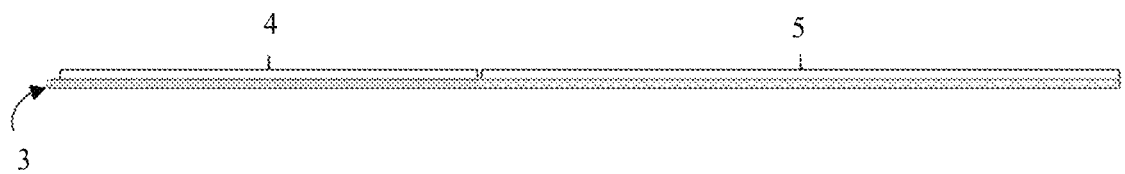
FIG. 1 is an overall schematic diagram of the optical fiber guidewire according to an example of the disclosure.

The present example provides an optical fiber guidewire. As shown in FIG. 1, the optical fiber guidewire includes at least one optical fiber 1 and a sleeve 2 surrounding the optical fiber 1. The sleeve 2 includes a functional section 3 capable of assisting the optical fiber 1 to emit and collect laser light, a guiding section 4 capable of bending and a supporting section 5 capable of supporting advancement of the functional section 3 and the guiding section 4 which are connected in sequence. The functional section 3, the guiding section 4 and the supporting section 5 are connected in sequence. The optical fiber guidewire is further provided with an asymmetric structure capable of directional bending of the optical fiber guidewire.

In this example, the optical fiber 1 may be an artificial fiber for transmitting light, and is located at an axis of the optical fiber guidewire. The optical fiber may be one, two or more, depending on specific circumstances, which is not limited in this disclosure.

The sleeve 2 is a tubular structure sheathed outside the optical fiber 1, and may be an equal-diameter sleeve 2 or a variable-diameter sleeve 2. When it is the equal-diameter sleeve 2, diameters of the functional section 3, the guiding section 4 and the supporting section 5 are equal. When it is the variable-diameter sleeve 2, outer diameters of the functional section 3, the guiding section 4 and the supporting section 5 increase sequentially. Specifically, the functional section 3 has the smallest diameter, and thus is more bendable compared to the guiding section 4 and the supporting section 5, which prompts the functional section 3 to guide the whole guidewire to advance along the bent blood vessel. The diameter of the supporting section 5 is larger than the diameter of the guiding section 4 and that of the functional section 3, which can make it have sufficient rigidity to provide forward driving force for the guiding section 4 and the functional section 3.

In this example, the optical fiber guidewire is further provided with an asymmetric structure capable of directional bending of the optical fiber guidewire to one side. The asymmetric structure is preferably an asymmetric tube wall structure of the sleeve 2, such as asymmetric slits and asymmetric tube walls thickness or shape. The configuration of the asymmetric structure can make the optical fiber guidewire easier to bend to one side, improve the bending performance and operability of the optical fiber guidewire. Therefore, it is easy to manipulate the optical fiber guidewire into smaller blood vessels or branch blood vessels with larger opening angles for detection and treatment.

Specifically, the sleeve 2 is a metal tube or a combination of a metal tube and a transparent tube. More specifically, the guiding section 4 and the supporting section 5 of the sleeve 2 are both metal tubes, and the functional section 3 is a metal tube or a transparent tube. The metal tube is preferably a hypotube, and the transparent tube is preferably made of a transparent polymer.

The optical fiber guidewire preferably has a total length of 2 m, a diameter preferably of 1.2 mm. An outer diameter of the sleeve 2 is 0.9-1.2 mm, preferably 1 mm, and an inner diameter of the sleeve 2 is 0.6-0.8 mm, preferably 0.8 mm. A length of the supporting section 5 is preferably 1.9 m, and a length of the guiding section 4 is preferably 0.1 m. An outer diameter of the optical fiber 1 is preferably 0.4 mm. In this example, the optical fiber guidewire has the diameter in order of millimeters, so that it can safely enter the smaller blood vessel for detection or treatment, avoid the damage of the guidewire to walls of blood vessels, and has a wide range of applications.

In the practices, the optical fiber 1 of the optical fiber guidewire can be connected to a pulsed detection laser and a waveform collector through an optical fiber combiner. An end, close to the supporting section 5, of the optical fiber guidewire can be connected to an attitude controller. The pulsed detection laser, the waveform collector and the attitude controller are all controlled by a control center. The control center sends control signals to the attitude controller, and the attitude controller controls the optical fiber guidewire to enter into or exit the body cavity or move in the body cavity based on the received control signals. The control center sends control signals to the pulsed detection laser, and the pulsed detection laser, based on the received control signals, emits pulsed laser light, and scatters the pulsed laser light into the body cavity via the optical fiber guidewire. The control center sends control signals to the waveform collector, and the waveform collector collects the delayed waveform of the scattered laser light based on the received control signals, and then by calculation, obtains information about the distance between the wall of the body cavity and the optical fiber including the relative position, whether there is a branch cavity in front of the fiber guidewire. The waveform collector feedbacks the above distance information to the control center and the attitude controller, so that the attitude and direction of subsequent movement of the guidewire can be controlled and adjusted, avoiding damage to the wall of the body cavity during the movement of the guidewire.

Therefore, the optical fiber guidewire provided in this example has good bending performance and operability, which makes the optical fiber guidewire easy to be manipulated and easy to enter the body cavity having a larger opening angle. Therefore, it can realize the self-guidance and flexible detection of the optical fiber guidewire in the body cavity, improving the therapeutic effect of minimally invasive interventional therapy.

Example 2

Figure 2:
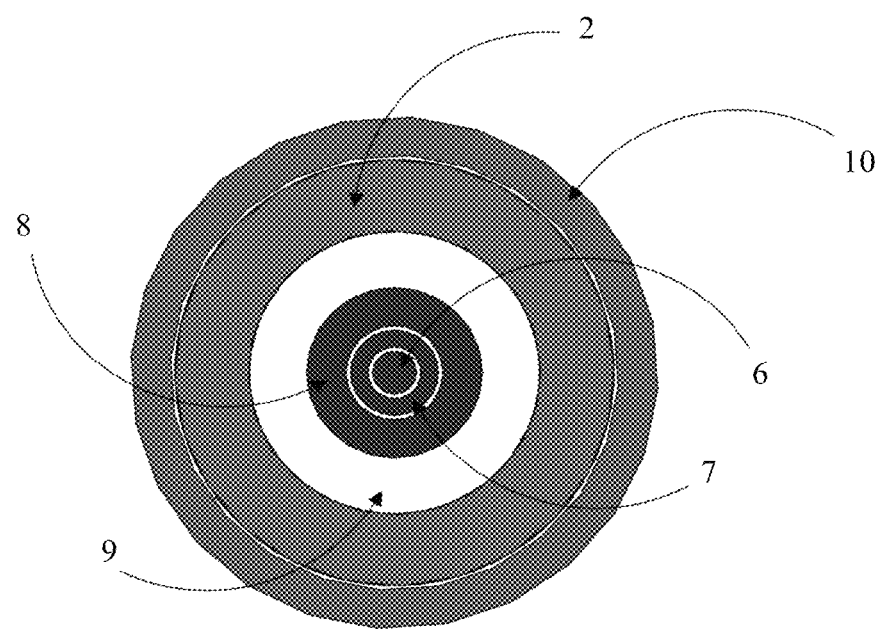
FIG. 2 is a cross-sectional schematic diagram of the optical fiber guidewire according to an example of the disclosure.

On the basis of example 1, the present example provides an optical fiber guidewire having a cross-sectional structure shown in FIG. 2.

In this example, the optical fiber guidewire has one optical fiber 1. A chamber 9 is provided between the optical fiber 1 and the sleeve 2. The optical fiber 1 includes a core fiber 6 capable of transmitting laser light, a cladding layer 7 capable of confining laser light transmission, and a sheath 8 capable of protecting the core fiber 6 and the cladding layer 7 that are successively arranged from inside to outside. There is a refractive index difference between the core fiber 6 and the cladding layer 7, so that light can be confined to transmit within the core fiber 6. The sheath 8 is preferably made of a polymer material to protect the optical fiber. The diameter of the core fiber 6 is preferably 0.2 mm. An outer surface of the sleeve 2 is also provided with a polymer layer 10 to protect the sleeve 2. In addition, a hydrophilic coating or a hydrophobic coating may be further provided outside the polymer layer 10. The hydrophilic coating can capture water to form a "gel-like" surface on the surface of the guidewire, reducing a resistance during the passage of the guidewire. The hydrophobic coating can resist water molecules to form a "waxy" surface, reducing friction during the passage, and enhancing the tracking of the guidewire.

Example 3

Figure 3:
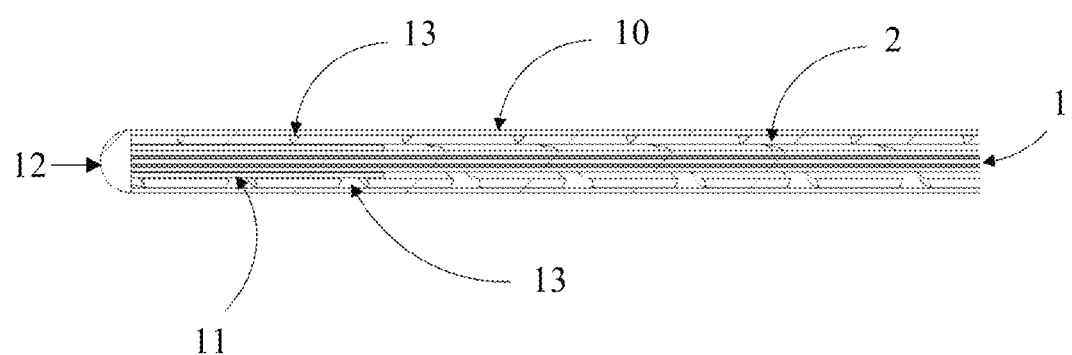
FIG. 3 is a side-sectional schematic diagram of the optical fiber guidewire according to an example of the disclosure.

On the basis of example 1 or 2, this example provides an optical fiber guidewire having a side-sectional structure of the guiding section 4 and the functional section 3 shown in FIG. 3.

Figure 4:
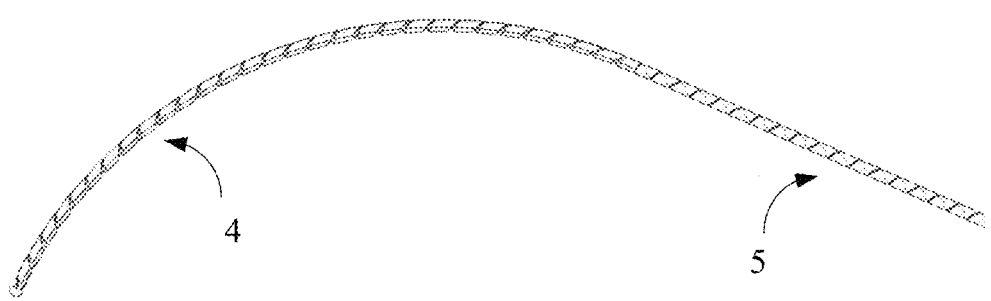
FIG. 4 is a schematic diagram of the optical fiber guidewire according to an example of the disclosure in a bending state.
Figure 5:
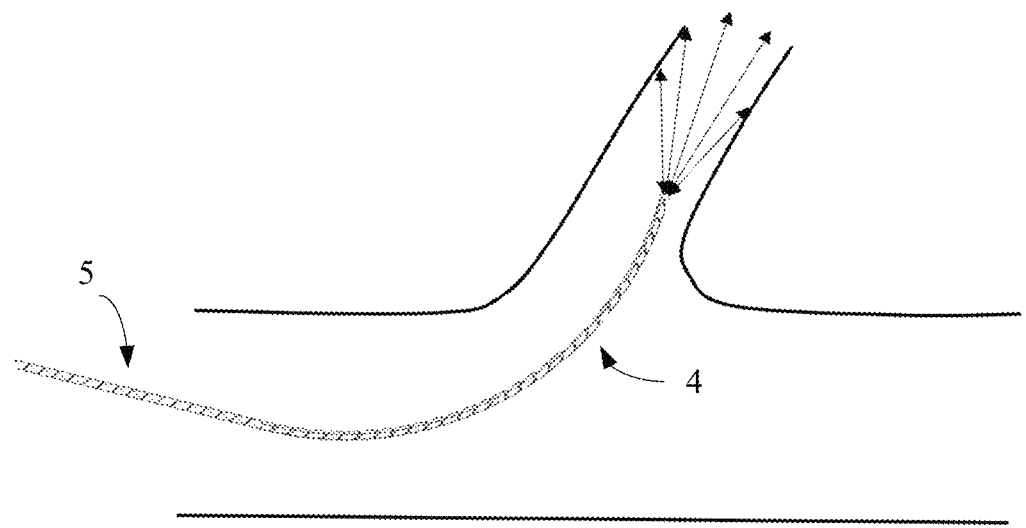
FIG. 5 is a schematic diagram of the optical fiber guidewire according to an example of the disclosure in a bending state.

In this example, the asymmetric tube wall structure is the asymmetric slit 13 opened on the sleeve 2. The asymmetric slit 13 is a spiral slit. The asymmetric slit 13 has different widths on two sides of the sleeve 2. The asymmetrical slit 13 is preferably opened on the guiding section 4 of the sleeve 2, as shown in FIGS. 4 and 5. The slit has a smaller width on one side, and has a larger width on the other side. Thereby, the guiding section 4 can be bent toward the side having the larger slit when force is applied, and the flexibility of the optical fiber guidewire can be improved.

The optical fiber guidewire also includes a developing ring 11. An inner wall of the developing ring 11 is fixedly connected to the optical fiber 1, preferably by means of adhesives. An outer wall of the developing ring 11 is fixedly connected to the sleeve 2, preferably by means of adhesives. The developing ring 11 is made of precious metals, such as gold, platinum, which can present clear images under the irradiation of X-rays, thereby assisting detection and treatment.

The sleeve 2 of the optical fiber guidewire is arranged a lens 12 capable of transmitting laser light, preferably a spherical light-emitting lens 12, which can be made of glass, gemstone or polymer, at an end of the functional section 3 away from the guiding section 4. The light from the optical fiber 1 can pass through the lens 12. External light can also be collected and returned to the optical fiber 1 through the lens 12 to assist in determining the position of the optical fiber guidewire, improving the self-guidance function of the optical fiber guidewire, and improving detection efficiency.

In the practices, the slit of the support section 5 has a width of preferably 0.1 mm, and a thread pitch of preferably 10 mm. The guiding section 4 has a thread pitch of preferably 2 mm, and the slit width on one side of the guiding section 4 is preferably 1 mm, and the slit width on the other side of the guiding section 4 is preferably 0.1 mm. The developing ring 11 has a length of preferably 5 mm, an outer diameter of preferably 0.8 mm, and an inner diameter of preferably 0.4 mm.

In the optical fiber guidewire provided in this example, the configuration of the spiral asymmetric slit 13 can further improve the bending performance and operability of the optical fiber guidewire. Therefore, the optical fiber guidewire can be easily manipulated and readily enter the body cavity with a large opening angle, realizing the self-guidance and flexible detection of the optical fiber guidewire in the body cavity, and improving the therapeutic effect of minimally invasive interventional therapy.

Example 4

Figure 6:
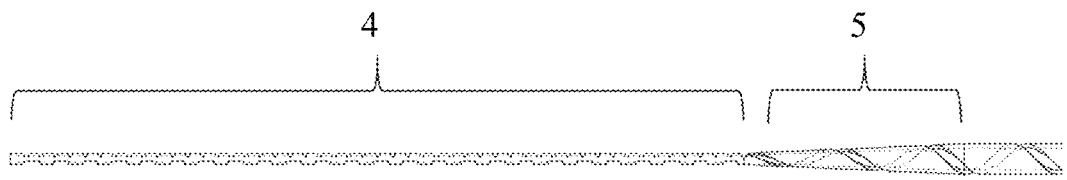
FIG. 6 is a schematic diagram of the asymmetric structure of the optical fiber guidewire according to an example of the disclosure.

On the basis of example 1 or 2, the present example provides an optical fiber guidewire having a side-sectional structure of the guiding section 4 and the supporting section 5 shown in FIG. 6.

In this example, the asymmetric tube wall structure is an asymmetric slit 13 opened on the sleeve 2, and the asymmetric slit 13 is a rectangular slit, i.e., the asymmetric slits 13 has different depths on two sides of the sleeve 2. The asymmetric slit 13 is preferably opened on the guiding section 4 of the sleeve 2. The asymmetric slit 13 of the guiding section 4 can make the optical fiber guidewire have asymmetric mechanical properties. It will be bent toward the side having the deeper depth when force is applied. Therefore, the optical fiber guide wire can easily and quickly enter the cavity with a larger opening angle. In addition, the rectangular slit is simple in the manufacture, is easy to be controlled during the use, and has high maneuverability and wide applications.

In addition, the optical fiber guidewire may also include a developing ring 11 and a lens 12. These components belong to the same concept as the related components in example 3. Related details can be seen from example 3, which will not be repeated here.

In the optical fiber guidewire provided in this example, the configuration of the rectangular asymmetric slit 13 can further improve the bending performance and operability of the optical fiber guidewire. Therefore, the optical fiber guidewire can easily enter the cavity with a large opening angle, realizing the self-guide and flexible detection of the optical fiber guidewire in the cavity, and improving the therapeutic effect of minimally invasive interventional therapy.

Example 5

Figure 7:
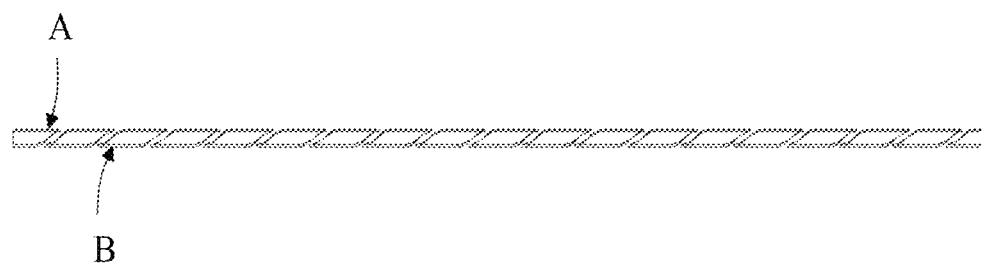
FIG. 7 is a schematic diagram of the asymmetric structure of the optical fiber guide wire according to an example of the disclosure.

On the basis of example 1 or 2, the present example provides an optical fiber guidewire having a side-sectional structure of the guiding section 4 shown in FIG. 7.

An asymmetric tube wall structure is formed by a wall thickness on one side of the sleeve 2 being smaller than a wall thickness of other side of the sleeve. Specifically, taking the sleeve 2 being a cylindrical sleeve 2 as an example, if it is divided into two half-cylindrical sleeves 2 along the cross-sectional diameter, as shown in FIG. 7, A represents the tube wall having a thinner thickness which is preferably 0.1 mm-0.3 mm, while B represents the tube wall having a thicker thickness which is preferably 0.3 mm-0.5 mm.

In the optical fiber guidewire provided in this example, the sleeve 2 has a thinner thickness on one side, and has a thicker thickness on the other side. When the guidewire is stressed, it can bend to the side of tube wall having the thinner thickness, so as to advance into the cavity with a larger opening angle.

In addition, the optical fiber guide wire may also include a developing ring 11 and a lens 12. These components belong to the same concept as the related components in example 3. Related details can be seen from example 3, which will not be repeated here.

In the optical fiber guidewire provided in this example, the configuration of the asymmetric tube wall structure can further improve the bending performance and operability of the optical fiber guidewire. Therefore, the optical fiber guidewire can be easily manipulated and can be easily enter the cavity with a large opening angle, realizing the self-guidance and flexible detection of the optical fiber guidewire in the cavity, and improving the therapeutic effect of minimally invasive interventional therapy.

Example 6

Figure 8:
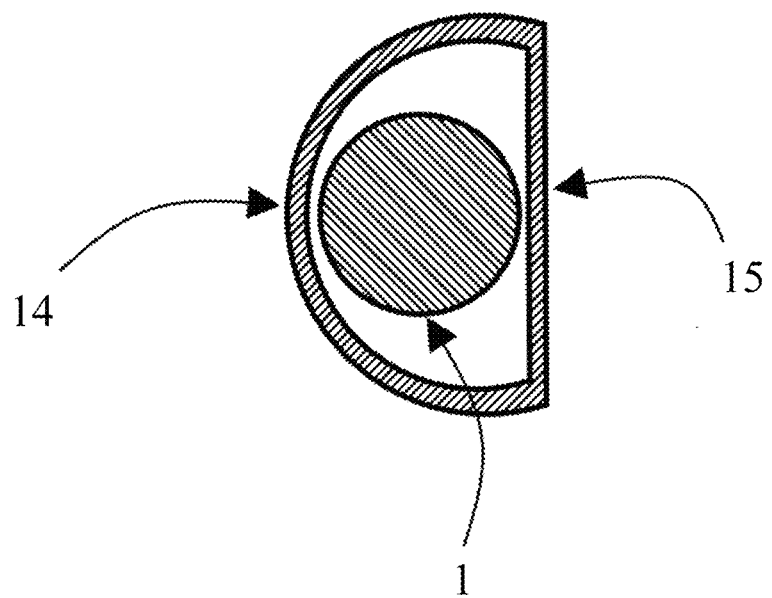
FIG. 8 is a schematic diagram of the asymmetric structure of the optical fiber guide wire according to an example of the disclosure.

On the basis of example 1 or 2, the present example provides an optical fiber guidewire having a cross sectional structure shown in FIG. 8.

The asymmetric tube wall structure is formed by a convex side 14 and a planar side 15 of the sleeve 2, or by a convex side 14 and a concave side of the sleeve 2. The convex side 14 has an arched structure.

Specifically, because the convex side 14 has the arched structure and its rigidity is relatively strong. when the optical fiber guidewire is stressed, it will be bent to the concave side or the planar side 15 opposite to the convex side 14, thereby making the optical fiber guidewire advance into the curved cavity more smoothly.

In addition, the optical fiber guide wire may also include a developing ring 11 and a lens 12. These components belong to the same concept as the related components in example 3. Related details can be seen from example 3, which will not be repeated here.

In the optical fiber guidewire provided in this example, the configuration of the asymmetric tubular structure can further improve the bending performance and operability of the optical fiber guidewire. Therefore, the optical fiber guidewire can be easily manipulated and can be easily enter the cavity with a larger opening angle, realizing the self-guidance and flexible detection of the optical fiber guidewire in the body cavity, and improving the therapeutic effect of minimally invasive interventional therapy.

Example 7

Figure 9:
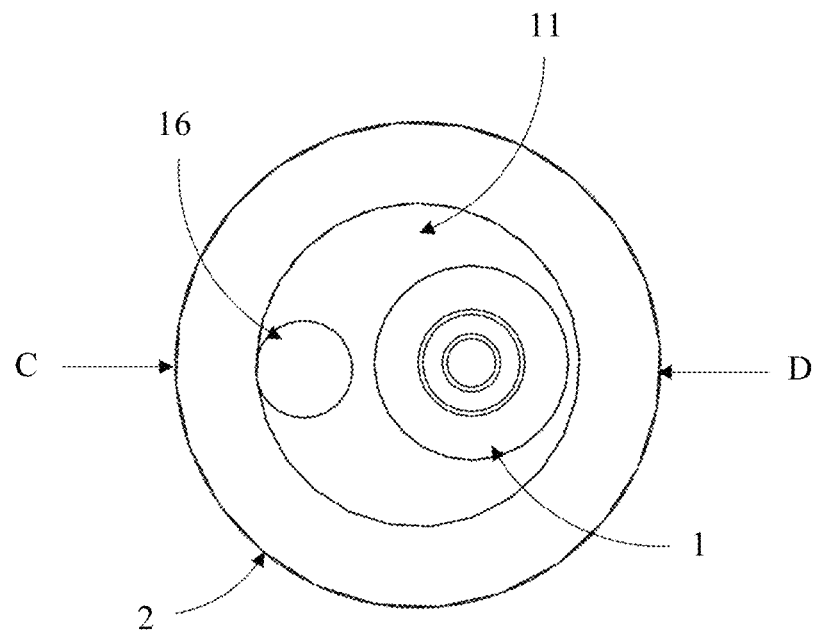
FIG. 9 is a cross-sectional schematic diagram of the optical fiber guidewire according to an example of the disclosure.

On the basis of anyone of examples 3-6, the present example provides an optical fiber guidewire having a cross sectional structure shown in FIG. 9.

In this example, the optical fiber guidewire has one optical fiber 1. The optical fiber guidewire further includes a power fiber 16. The power fiber 16 and the optical fiber 1 are both located within the sleeve 2. A length direction of the power fiber 16 and a length direction of the optical fiber 1 are both parallel to a length direction of the sleeve. The power fiber 16 is fixedly connected to one side of the sleeve 2. In the case that the asymmetric tube wall structure is an asymmetric slit 13, the power fiber 16 is fixedly connected to the side with the larger slit. In the case that the asymmetric tube wall structure is asymmetrical tube wall thickness, the power fiber 16 is fixedly connected to the thinner side of the tube wall. In the case that the asymmetric tube wall structure is formed by the shape of the sleeve 2, the power fiber 16 is fixedly connected to the concave portion or the planar portion 15. In FIG. 9, C indicates the side with the larger slit, and D indicates the side with the small slit. The power fiber 16 is preferably a metal wire, which can be fixedly connected to the sleeve 2 by means of gluing, welding, or the like.

The power fiber 16 can provide tensile force to the optical fiber guidewire. By tightening the power fiber 16, the tensile force is transmitted to the side with the larger slit, the side with the thinner thickness, concave side, or planner side 15, which results in the shrinking of this side, thereby bending the guiding section 4, and improving the bending flexibility and bending amplitude of the optical fiber guidewire.

In the optical fiber guidewire provided in this example, the configuration of the power fiber 16 further improves the bending performance and operability of the optical fiber guidewire. Therefore, the optical fiber guidewire can be easily manipulated and can readily enter the body cavity with a larger opening angle, realizing the self-guidance and flexible detection of the optical fiber guidewire in the body cavity, and improving the therapeutic effect of minimally invasive interventional therapy.

Example 8

Figure 10:
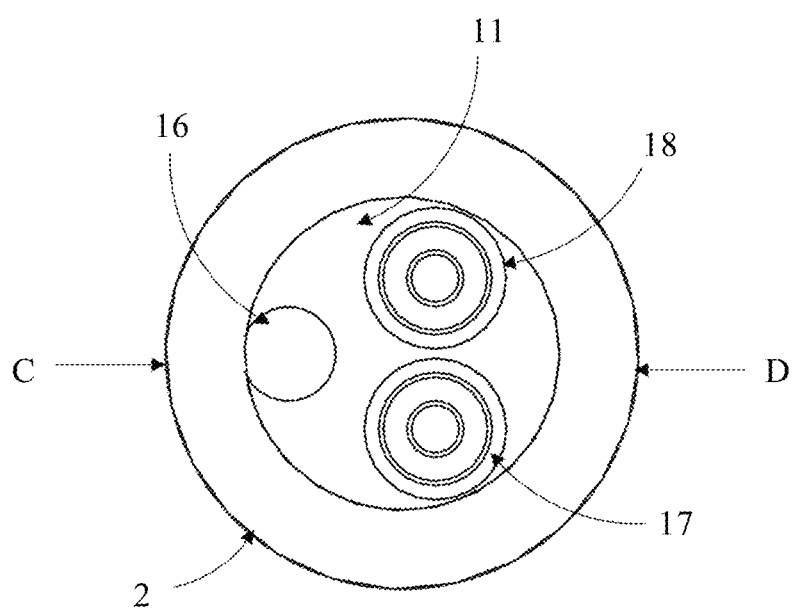
FIG. 10 is a cross-sectional schematic diagram of the optical fiber guidewire according to an example of the disclosure.

On the basis of example 7, this example provides an optical fiber guidewire having a cross-sectional structure shown in FIG. 10 in which C represents the side with the larger slit, and D represents the side with the smaller slit.

In this example, the optical fiber guidewire has two optical fibers 1, i.e., a detecting fiber 17 and a treating fiber 18, respectively. The detecting fiber 17 is used to provide pulsed detecting laser light, and the treating fiber 18 is used to provide treating laser light.

The detecting fiber 17 can be connected to the pulsed detection laser. The pulsed detecting laser may emit pulsed detecting laser light through the detecting fiber 17 to assist in determining the position and direction of advancement of the fiber guidewire. Preferably, laser light from the detecting fiber 17 passes through the lens 12 for collimated emission. The distance between the top end of the detecting fiber 17 and the lens 12 is a focal length of the lens 12. For example, the diameter of the functional section 3 of the sleeve 2 is 1 mm, the exit angle of the optical fiber is ±15 degrees, the spot diameter is 2 mm from the exit end face of the optical fiber, and then the focal length of the lens 12 is 2 mm.

Figure 11:
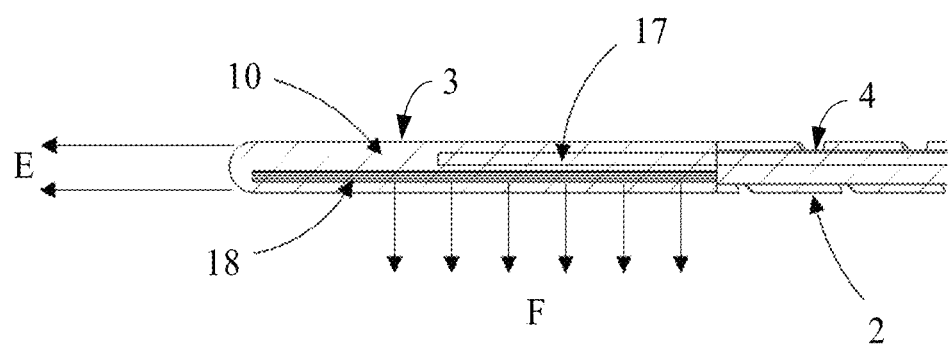
FIG. 11 is a side-sectional schematic diagram of the optical fiber guidewire according to an embodiment of the disclosure.
Figure 12:
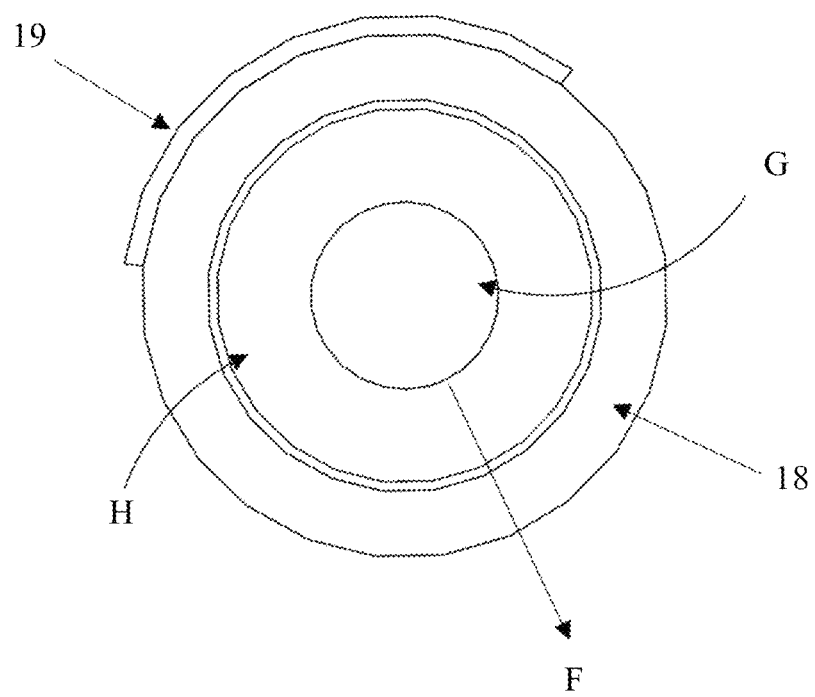
FIG. 12 is a cross-sectional schematic diagram of the optical fiber guidewire according to an example of the disclosure.

The treating fiber 18 may be connected to the treatment laser. The treating laser may emit treating laser through the treatment fiber 18 to perform laser irradiation treatment on the lesion sites. The treating fiber 18 has the function of lateral light emission, so the functional section 3 of sleeve 2 of the optical fiber guidewire is preferably a transparent tube. In FIGS. 11 and 12, E represents the detecting laser, F represents the treating laser, G represents a front face of the treating fiber 18, and H represents the rear face of the treating fiber 18. The rear face of the treating fiber 18 is larger than the front face thereof. The treatment laser enters from the rear face of the treating fiber 18. As the diameter of the treating fiber 18 gradually decreases, the confining on the laser light transmitted in the fiber gradually decreases, and the treating laser light escapes from the core fiber. In addition, a metal reflective film 19 is coated on one side of the treating fiber 18, is used for reflecting the laser light scattered in the direction of the detecting fiber 17 and emitting it from the treatment side.

In the optical fiber guidewire provided in this example, the configuration of the detecting fiber and treating fiber can further improve the detection performance and treatment performance of the optical fiber guidewire, from different aspects and points, expend the application range of the optical fiber guidewire, and increase the flexibility of the optical fiber guidewire.

Example 9

Figure 13:
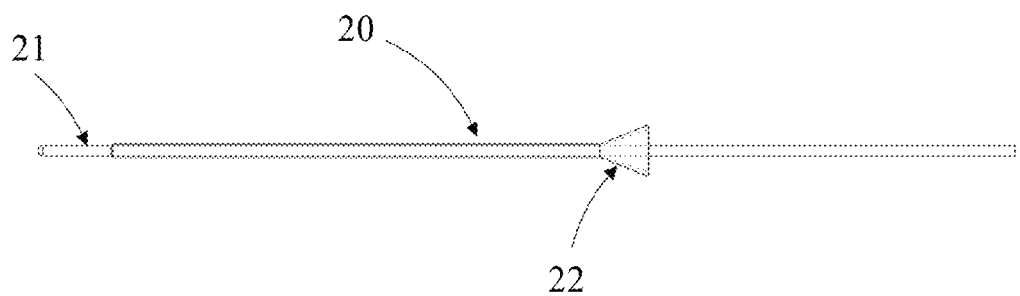
FIG. 13 is an overall schematic diagram of the optical fiber guidewire according to an example of the disclosure.

On the basis of anyone of examples 1-8, the present example provides an optical fiber guidewire having a structure shown in FIG. 13.

In this example, the optical fiber guidewire is sheathed with a guide tube 20. The guiding tube 20 is connected to a guiding rod 21 at an end close to the functional section 3 and is sheathed with a wing 22. The guiding rod 21 and the guiding tube 20 are made of flexible materials such as medical polymers, plastics, rubber, etc., and have a certain deformation ability.

In the practices, the guiding rod 21 can be inserted into the human body cavity, and the guiding tube 20 can be inserted into the human body cavity along the guiding rod 21. Then, the guiding rod 21 can be withdrawn, and the optical fiber guidewire can be inserted into the human body cavity along the guiding tube 20, thereby avoiding the irritation and damage to the cavity mucosa caused by the movement of the guidewire in the body cavity.

Figure 14:
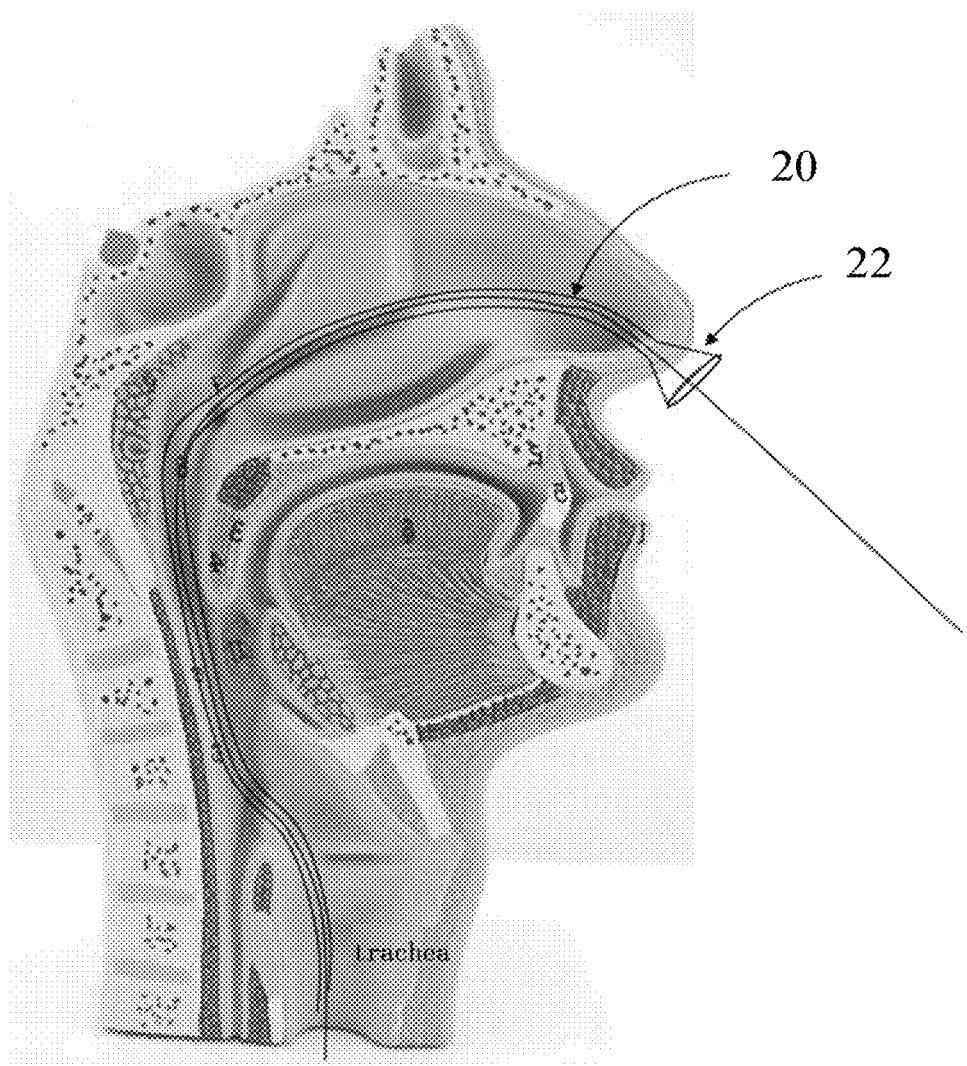
FIG. 14 is a schematic diagram of the optical fiber guidewire in use according to an embodiment of the disclosure.

Taking photodynamic therapy of the lungs as an example, as shown in FIG. 14, when performing photodynamic therapy of the lungs, the guiding rod 21 is inserted through the nasal cavity or oral cavity (the nasal cavity in this figure), and is inserted into the trachea through the throat. The guiding tube 20 is inserted along the guiding rod 21, and the end of the guiding tube 20 enters the trachea. Then the guiding rod 21 is drawn out, and a channel is formed by the guiding tube 20. At this time, the optical fiber guidewire is inserted into the guiding tube 20 and enters the trachea from the guiding tube 20. When the optical fiber guidewire is moving, the guiding tube 20 is stationary, thereby avoiding repeated stimulation to the throat caused by the movement of the guidewire.

The optical fiber guidewire can enter the bronchus through the trachea under the control of the attitude controller (it can be guided independently or in combination with the guidance of a small amount of X-ray), and then enters the lower bronchus through the attitude adjustment of the head portion under the guidance of detection laser to the head portion, until it reaches the vicinity of the tissue to be treated. Then, the detection laser is turned off, and the treatment laser (for example, red light at 660 nm or blue light at 400 nm) is turned on, and photodynamic therapy is performed on the lung tissue. After the treatment, the optical fiber guidewire and the guide tube 20 are drawn out.

In the optical fiber guidewire provided in this example, the configuration of the guiding tube 20, the guiding rod 21, and the wing 22 can effectively avoid damage to the human cavity caused by the optical fiber guidewire, and improve the patient's experience.

Example 10

Figure 15:
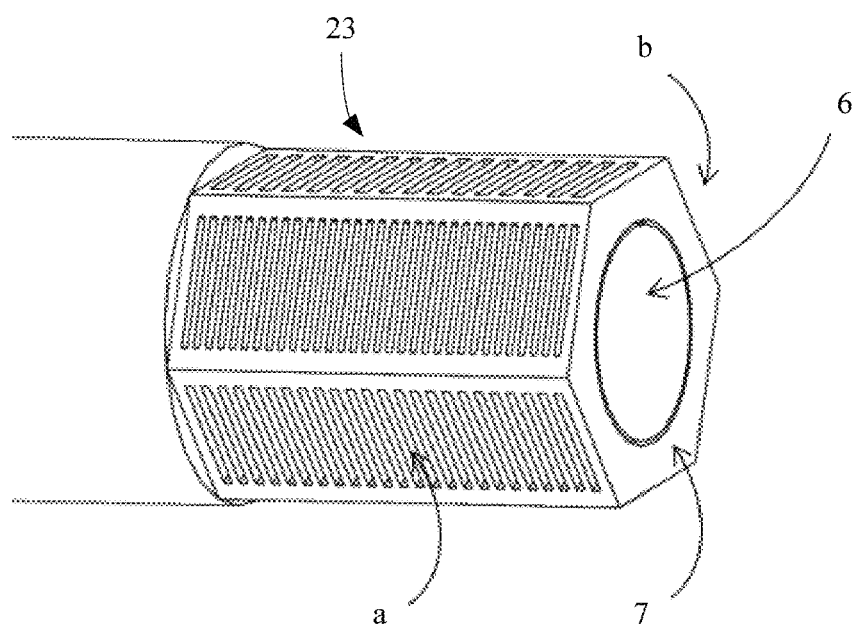
FIG. 15 is a schematic diagram of a partial structure of the optical fiber guidewire according to an embodiment of the disclosure.

On the basis of example 1 or 2, the present example provides an optical fiber guidewire shown in FIG. 15. The functional section 3 of the optical fiber 1 may also be provided with at least one grating assembly 23. The grating assemblies 23 are sleeved on the optical fiber 1 at intervals, and are arranged longitudinally along the optical fiber 1.

Specifically, the optical fiber 1 includes a core fiber 6 located at the axis and the cladding layer 7 wrapped around the core fiber 6. The grating assemblies 23 are sleeved outside the cladding layer 7 at intervals. Each of grating assemblies 23 is in shape of hollow prism. The grating assembly 23 includes a plurality of gratings with different periods, and each grating constitutes a side surface of the grating assembly. When pulsed lasers with multiple wavelengths are transmitted into the optical fiber, the wavelengths of the pulses coupled from different gratings are different. The number of gratings of the grating assembly is the same as the number of side surfaces of the prism. For example, when the grating assembly is in the shape of a hollow hexagonal prism, it is composed of 6 gratings with different periods. In the practices, there may be three grating assemblies, and each of the grating assemblies has six gratings.

The grating is an optical device that is specified for emitting and collecting laser light, and is composed of a large number of parallel slits having equal width and equal spacing. In the optical fiber guide wire described in this example, the laser light transmitted by the optical fiber guidewire can be scattered into the cavity through the grating assemblies 23, and the retro-reflected laser light can also be collected through the grating assemblies 23 to determine the position of the optical fiber guidewire in the body cavity and to accurately determine the direction of subsequent movement of the optical fiber guidewire.

Referring to FIG. 15, a and b represent two gratings in opposite directions. In the practices, laser light from by grating a is scattered by the cavity wall and then coupled into the optical fiber via the grating a, while the laser light from by grating b is scattered by the cavity wall, and then coupled into the optical fiber via grating b. In the case of a branch cavity at grating a, the distance between the grating a and the cavity wall is greater than the distance between the grating b and the cavity wall, and thus the time for collecting the scattered pulses by grating a is lagging behind that by grating b. In the case of a branch cavity at grating b, the distance between the grating b and the cavity wall is greater than the distance between grating a and the cavity wall, and thus the time for collecting the scattered pulse by grating b is lagging behind that by grating a. in this way, by analyzing the waveform of the scattered echo, the branch morphology of the cavity can be obtained, thereby guiding the guiding section 4 to bend to entry into the branch cavity. By analyzing the waveform of the grating echo in different directions, the situation of the branch cavity where each grating is located can be determined, thereby providing more detailed judgment data for the more complicated shape of passage of the cavity, so as to improve the efficiency of movement of the guidewire.

Example 11

The disclosure also provides a detection system with the optical fiber guidewire, including:

an optical fiber guidewire according to any of examples 1-10;

a control center arranged for sending control signals to an attitude controller, a pulsed detection laser, a waveform collector, and a treatment laser to control a start-up, operation or shutdown of the attitude controller, the pulsed detection laser, the waveform collector, and the treatment laser;

the attitude controller arranged for receiving signals sent by the control center and distance information, and driving the optical fiber guidewire to entry or exit a body cavity or move in the body cavity;

the pulsed detection laser arranged for receiving signals sent by the control center, and sending out pulsed laser light which is transmitted to the body cavity through the optical fiber guidewire and forms laser scattering within the body cavity;

the waveform collector arranged for receiving signals sent by the control center, collecting and analyzing a delayed waveform of scattered laser in the body cavity, to obtain the distance information about a distance between a wall of the body cavity and the optical fiber guidewire, and feedback the distance information to the control center.

Figure 16:
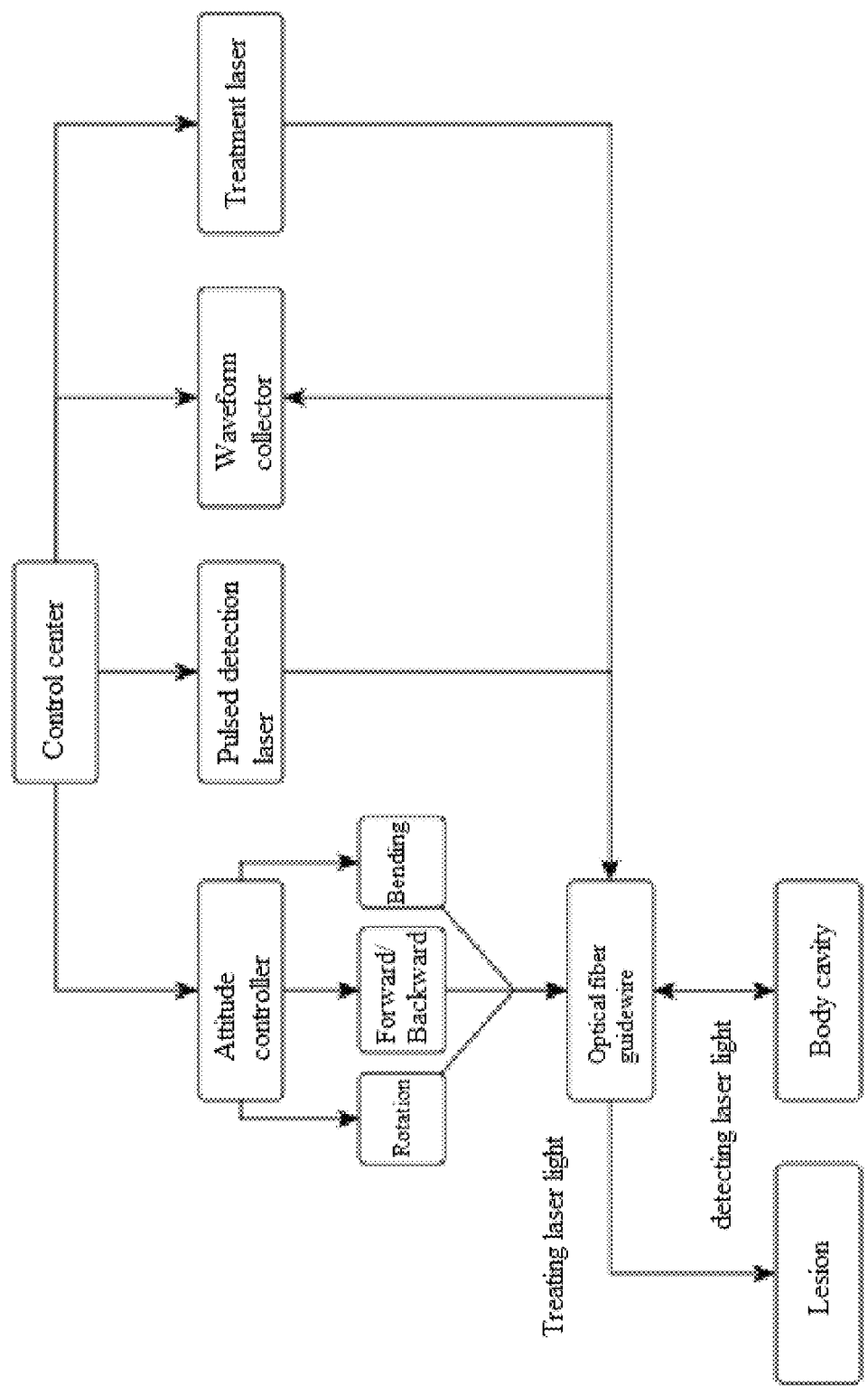
FIG. 16 is a working principle diagram of the detection system with the optical fiber guidewire according to an embodiment of the disclosure.

As shown in FIG. 16, the optical fiber 1 of the optical fiber guidewire may be connected to the pulsed detection laser, the waveform collector, and the treatment laser through an optical fiber combiner. An end, close to the supporting section 5, of the optical fiber guidewire can be connected to the attitude controller. The pulsed detection laser, the waveform collector and the attitude controller are all controlled by the control center.

The control center sends control signals to the attitude controller, and the attitude controller controls the optical fiber guidewire to enter into or exit the body cavity or move in the body cavity based on these control signals. For example, a linear stepping motor may be used for driving the guidewire to move forward or backward; a stepper motor, steering gear or the like may be used for driving the rotation of the guidewire by the rotation; a linear stepping motor may be used for pulling the optical fiber, and driving the guiding section 4 to bend to the side with the larger slit.

The control center sends control signals to the pulsed detection laser, and the pulsed detection laser, based on the received control signals emits pulsed laser light, and scatters the pulsed laser light into the body cavity via the optical fiber guidewire. The control center sends control signals to the waveform collector, and the waveform collector collects the delayed waveform of the scattered laser light according to the received control signals, and then by calculation, obtains information about the distance between the wall of the cavity and the optical fiber including the relative position, whether there is a branch cavity in front of the fiber guidewire.

Specifically, the detection laser emits a pulse sequence with a wavelength of 1064 nm, a repetition frequency of 100 Hz, and a pulse length of 1 ps. The pulse sequence is transmitted by the optical fiber guidewire, exited from the top end of the guidewire, scattered on the wall of the cavity, and collected by the optical fiber to return the waveform collector. The waveform collector has a high-speed electro-optical detector for collecting the echo waveform and analyzing the time period of the waveform, so as to determine the distance between the top end of the guidewire and the wall of the cavity.

Figure 17:
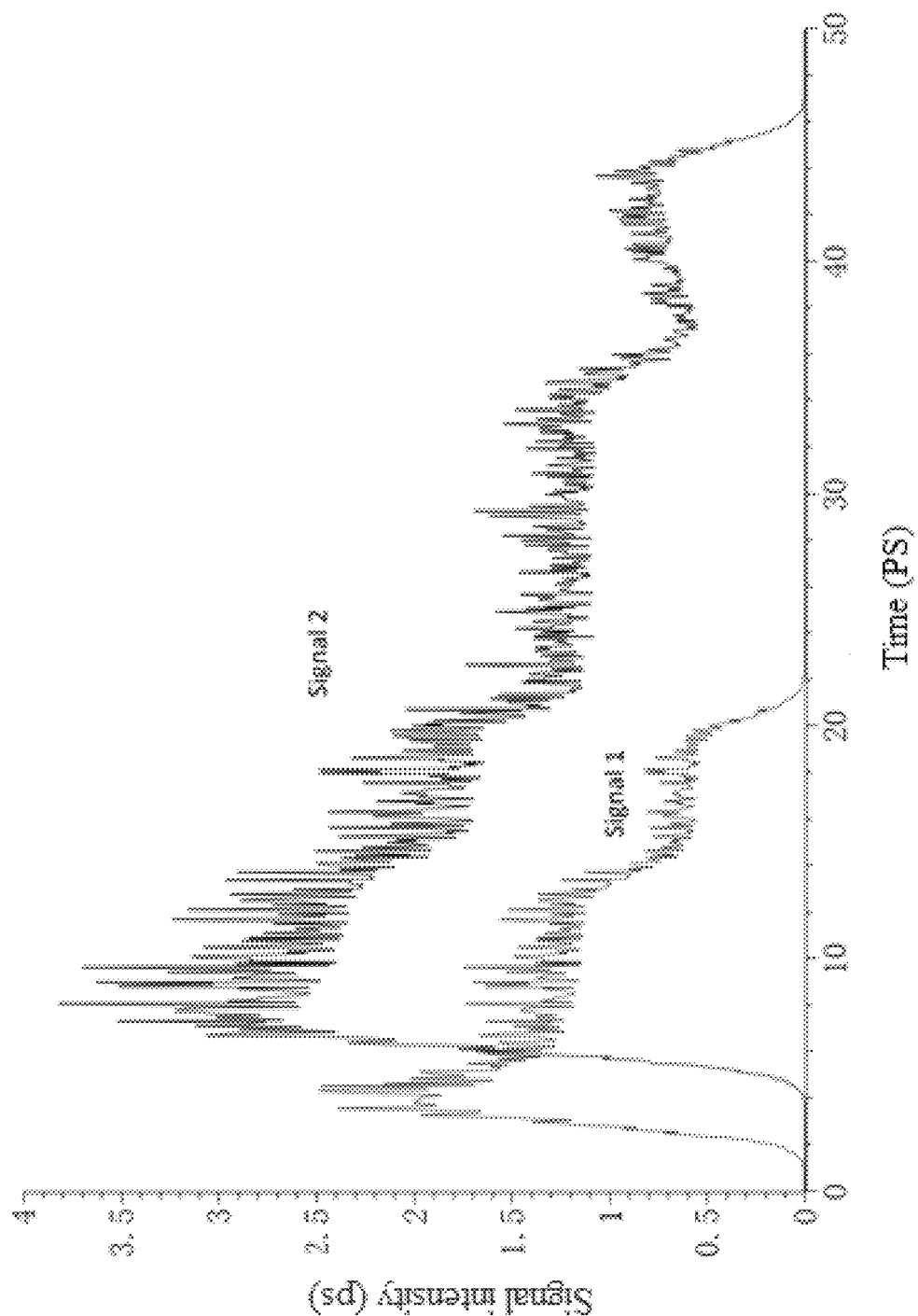
FIG. 17 is a delayed waveform of superimposed laser pulse according to an embodiment of the disclosure.

As shown in FIG. 17, picosecond pulsed laser, such as 1 picosecond pulsed laser may be used. When the wall of the cavity is in front of the top end of the guiding section 4, the scattered echo is denoted as "Signal 1", while when the top end of the guiding section 4 faces a branch cavity 9 (for example, the lower bronchus), the scattered echo is denoted as "Signal 2" with a longer waveform, due to the farther distance from the scattering wall. By analyzing the time period of the scattered echo, the distance between the top end of the guiding section 4 and the wall of the cavity can be obtained. The waveform collector feedbacks the information about the above distance to the control center and the attitude controller, so that the attitude and the direction of subsequent movement of the guidewire can be controlled and adjusted.

In addition, the detection system with the optical fiber guidewire further includes the treatment laser arranged for receiving the signals sent by the control center, and emitting a laser light for treating according to the control signals, to scatter to a lesion site to be treated through the optical fiber, so as to perform the treatment on the lesion site.

In the detection system with the optical fiber guidewire provided in this example, the control center can send control signals to other components to coordinate and control the cooperation among these components. The attitude controller can control the optical fiber guidewire to enter or exit the body cavity or move in the cavity, which improves the flexibility of the optical fiber guidewire during use. Through the cooperation of the pulsed detection laser, the waveform collector and the fiber guidewire, the relative position of the optical fiber guidewire and the wall of the cavity can be determined by the delay of the laser light, and then the subsequent attitude and moving direction of the optical fiber guidewire can be accurately determined. Therefore, the detection efficiency can be increased. Furthermore, the treatment lase can emit a laser light for treating to irradiate a lesion site through the optical fiber guidewire, thereby improving the flexibility and efficiency of treatment.

Example 12

This example provides a detection method using the optical fiber guidewire. The detection method is used in the detection system with the optical fiber guidewire of example 11. The method includes the following step S1 to step S5.

At step S1, the control center receives control instructions, and sends control signals to the attitude controller and the pulsed detection laser based on the control instructions.

At step S2, the attitude controller receives the control signals sent by the control center, and drives the optical fiber guidewire into the cavity based on the control signal.

At step S3, the pulsed detector receives the control signals sent by the control center, emits pulsed laser light, and scatters the pulsed laser light into the cavity via the optical fiber guidewire.

At step S4, the optical fiber guidewire receives a reflected pulsed laser light and sends the reflected pulsed laser light to the waveform collector. Based on the reflected pulsed laser light, the waveform collector determines a position of the optical fiber guidewire in the cavity.

At step S5, the attitude controller controls a subsequent movement of the optical fiber guidewire based on the position of the optical fiber guidewire in the cavity, until the optical fiber guidewire reaches target site and exits the cavity after completing detection.

In addition, after the optical fiber guidewire reaches the target site, the control center sends control signals to the treatment laser, and the treatment laser emits treatment laser light which is scattered to the target site through the optical fiber guidewire to treat the target site.

The detection method using the optical fiber guidewire provided by this example realizes the intelligent and automatic guidance of the optical fiber guidewire in the cavity through the cooperation of the control center, the attitude controller, the pulsed detector, the optical fiber guide wire and the waveform collector. In addition, through the cooperation of the control center, the optical fiber guidewire and the treatment laser, the laser irradiation treatment can be performed to the lesion sites of the patient with high treatment efficiency and good effect, thereby improving flexibility in use and application range of the optical fiber guidewire.

In the description, the expressions "equal", "same" and the like are not strictly mathematical and/or geometrical limitations, and also include tolerances in manufacturing or use that can be understood by those skilled in the art.

Unless otherwise specified, the numerical range herein includes not only the entire range within its two endpoints, but also several sub-ranges contained therein.

Although preferred embodiments and examples of the present disclosure have been shown in detail with reference to drawing, the present disclosure is not limited to the above embodiments and examples. Various modifications may be made without departing from the concept of the present disclosure, within the knowledge possessed by those skilled in the art.

What is claimed is:

1. A detection system comprising:
   an optical fiber guidewire;
   a control center arranged for sending control signals to an attitude controller, a pulsed detection laser, a waveform collector and a treatment laser to control a start-up, operation or shutdown of the attitude controller, the pulsed detection laser, the waveform collector and the treatment laser;
   the attitude controller arranged for receiving signals sent by the control center and distance information, and driving the optical fiber guidewire to entry or exit a body cavity or move in the body cavity;
   the pulsed detection laser arranged for receiving signals sent by the control center, and sending out pulsed laser light which is transmitted to the body cavity through the optical fiber guidewire and forms laser scattering within the body cavity;
   the waveform collector arranged for receiving signals sent by the control center, collecting and analyzing a delayed waveform of scattered laser in the body cavity, to obtain the distance information about a distance between a wall of the body cavity and the optical fiber guidewire, and feedback the distance information to the control center.

2. A detection method using the optical fiber guidewire, according to claim 1, the detection method comprising:
   by the control center, receiving control instructions, and sending control signals to the attitude controller and the pulsed detection laser based on the control instructions;
   by the attitude controller, receiving the control signals sent by the control center, and driving the optical fiber guidewire into a body cavity based on the control signals;
   by a pulsed detector, receiving the control signals sent by the control center, and emitting pulsed laser light; then scattering the pulsed laser light into the body cavity via the optical fiber guidewire;
   by the optical fiber guidewire, receiving a reflected pulsed laser light, and sending the reflected pulsed light, to the waveform collector; then by the waveform collector, based on the reflected pulsed laser light, determining a position of the optical fiber guidewire in the body; and
   based on the position of the optical fiber guidewire in the body cavity, controlling a subsequent movement of the optical fiber guidewire by the attitude controller, until the optical fiber guidewire reaches a target site and exits the cavity after completing detection.

3. The detection system according to claim 1, wherein the optical fiber guidewire comprises:
   an optical fiber; and
   a sleeve surrounding the optical fiber, the sleeve comprising:
   a functional section assisting the optical fiber to emit and collect laser light;
   a guiding section capable of bending; and
   a supporting section supporting an advancement of the functional section and the guiding section,
   wherein the functional section, the guiding section and the supporting section are connected in sequence; and
   the optical fiber guidewire is provided with an asymmetric structure capable of directional bending of the optical fiber guidewire.

4. The detection system according to claim 3, wherein the optical fiber comprises, from inside to outside:
   a core fiber transmitting laser light;
   a cladding layer confining transmission of laser light;
   a sheath protecting the core fiber and the cladding layer; and
   a lens transmitting laser light arranged at an end away from the guiding section, of the functional section of the sleeve.

5. The detection system according to claim 3, further comprising:
   a developing ring located between the optical fiber and the sleeve; and
   an inner wall of the developing ring is fixedly connected to the optical fiber, and an outer wall of the developing ring is fixedly connected to the sleeve.

6. The detection system according to claim 3, further comprising a power fiber,
  wherein the power fiber and the optical fiber are both located within the sleeve; and
  a length direction of the power fiber and a length direction of the optical fiber are both parallel to a length direction of the sleeve.

7. The detection system according to claim 3, wherein the optical fiber is a detecting fiber, or the optical fiber is formed by combining the detecting fiber and a treating fiber.

8. The detection system according to claim 3, wherein the sleeve is a metal tube, or a combination of a metal tube and a transparent tube.

9. The detection system according to claim 3, wherein the asymmetric structure is an asymmetric tube wall structure of the sleeve.

10. The detection system according to claim 3, wherein the optical fiber guidewire is sheathed with a guiding tube.

11. The detection system according to claim 8, wherein the guiding section and the supporting section of the sleeve are both the metal tube, and the functional section is the metal tube or the transparent tube.

12. The detection system according to claim 9, wherein the asymmetric tube wall structure is an asymmetric slit opened on the guiding section of the sleeve, an asymmetric tube wall thickness of the sleeve, or a shape of the sleeve.

* * * * *